United States Patent [19]

Schulmeyer

[11] Patent Number: 4,498,865

[45] Date of Patent: Feb. 12, 1985

[54] PROCEDURE FOR FIRING DENTAL PORCELAIN ON METAL

[75] Inventor: Herbert G. Schulmeyer, Messel, Fed. Rep. of Germany

[73] Assignee: Dentsply Research & Development Corp., Milford, Del.

[21] Appl. No.: 526,022

[22] Filed: Aug. 24, 1983

[30] Foreign Application Priority Data

Aug. 25, 1982 [DE] Fed. Rep. of Germany ....... 3231546

[51] Int. Cl.$^3$ ............................................... F26B 9/12
[52] U.S. Cl. ...................................................... 432/18
[58] Field of Search ............................ 432/18; 264/18; 427/374.1, 444

[56] References Cited

U.S. PATENT DOCUMENTS

| | | | |
|---|---|---|---|
| 1,924,267 | 8/1933 | Alley | 264/66 |
| 2,646,608 | 7/1953 | Boeke | 264/66 |
| 2,779,082 | 1/1957 | Scharf | 264/66 |
| 3,151,851 | 10/1964 | Negley | 432/205 |
| 3,213,161 | 10/1965 | Craig | 264/66 |
| 3,247,293 | 4/1966 | Myerson | 264/16 |
| 3,541,193 | 11/1970 | Adams | 264/66 |
| 3,594,456 | 7/1971 | Berenshtein | 264/66 |
| 4,109,031 | 8/1978 | Marscher | 432/18 |
| 4,254,070 | 3/1981 | Yodogawa et al. | 264/66 |

FOREIGN PATENT DOCUMENTS

0087111 A2 2/1983 European Pat. Off. .
8204464 2/1982 Fed. Rep. of Germany .

OTHER PUBLICATIONS

Dorsch, P.: Messmethode zur Spannungsberechnung in Metall/Porzellan-Verbundkorpern. Ber. Dtsch. Keram. Ges. 56, pp. 328-331, (1979).

Primary Examiner—John J. Camby
Attorney, Agent, or Firm—Edward J. Hanson, Jr.; C. Hercus Just

[57] ABSTRACT

Disclosed is a method for producing dental prostheses of the dental porcelain fused to metal type, in particular, the temperatures employed to fire and cool the prostheses are disclosed with a new tempering temperature disclosed during cool down. The tempering temperature is preferably the temperature with approximately the maximum rate of crystallization out of the glass phase of the feldspathic dental porcelain.

A furnace is also disclosed having a heatable firing chamber, a firing platform, a firing platform socket, and control means that include a means for positioning the platform and adjusting the temperature. The furnace control means is programmed by a keyboard feeding a microcomputer, which controls separate programmable elements to control the furnace.

12 Claims, 2 Drawing Figures

PROCEDURE FOR FIRING DENTAL PORCELAIN ON METAL

BACKGROUND OF THE INVENTION

This invention relates to firing dental porcelain on metal in manufacturing dental prostheses and in particular to the cool-down procedure.

The procedure for firing dental porcelain to fuse the dental porcelain with the metal in manufacturing dental prostheses producing good aesthetic and performance characteristics has been known for a long time. The bonding system for fusing the dental porcelain to metal begins essentially with the application of one or more layers of unfused dental porcelain material to a metal support or substrate. The dental porcelain is conventionally applied in several layers of varying compositions and shades. Usually the initial layers are dental opaquing porcelains, and then there is a middle dental body porcelain and/or stains and then a covering enamel. Each individual layer is usually fired and appropriate tooth anatomy is carved in each layer. Therefore, it will be understood that the dental porcelain materials are fused on the substrate which may be a crown or bridge substructure made of a special precious metal alloy, a semi-precious metal alloy, or a non-precious alloy by means of several successive firing processes. The firing temperature for each layer's successive firing is usually between 900° C. and 980° C. The firing is usually carried out under a temporary partial vacuum in a firing chamber. The final firing is generally referred to as a glaze firing.

The thermal expansion of the bonding alloys during multiple heating and cooling phases between room temperature and approximately 980° C. is usually relatively constant. However, the highly feldspathic materials of the usual dental porcelains which are fused to the metal can have considerable variation in performance because of e.g. the crystallization in the glass ceramic system $K_2O.Al_2O_3.SiO_2$ by forming leucite. The problem is specifically noted here with regard to these highly feldspathic materials which are present in the preferred dental porcelains. It is understood that in the temperature range of approximately 600° to 900° C. crystallization occurs, and dependent on this crystallization, an increase of heat expansion results, dependent on temperature and time.

The repetitious heating and/or cooling modes of the various build-up procedures tend to cause compressive or tensile stresses which can lead to chippings, fissures, or cracks at the porcelain interfaces with the metal or alloy. This can result in an unsatisfactory product necessitating a remake.

The achievement of desirable low compressive stress in dental porcelain/metal bonding systems is additionally complicated by the fact that the variety of alloys has increased considerably in recent years. The coefficient of thermal expansion can vary between 138 to $154 \times 10^{-7}/K$. (K.=Kelvin) over the temperature interval of 25° to 600° C. customarily measured. Therefore, the danger of strong compressive or tensile stresses in dental porcelains fused to metal in such bonding systems is increased and failures caused by cracks or chipping of the veneering layers are increasingly likely.

During the cooling phase of the firing procedure used to manufacture a dental porcelain fused to metal prostheses, there arises a temperature gradient in progression from the dental porcelain's face or outer surface inwardly to the metal. This temperature gradient is higher when rapid cooling takes place. This means that especially in the dental porcelain solidification temperature range, the metal normally shows a lower temperature than the dental porcelain veneer. The stresses in the fused cold dental porcelain to metal interface appear to be substantially directly proportional to this difference in temperature.

It is an object of the present invention to provide a porcelain metal prostheses that will meet clinical test and provide a long, useful prostheses life.

It is another object of the present invention to provide a dental porcelain/metal prostheses having no inherent tensions that would produce cracks or chips.

It is a further object of the present invention that at room temperature the dental porcelain is under essentially low compressive stress.

A still further object of the present invention is to improve the manufacturing procedure for producing dental porcelain veneer prostheses to eliminate or ameliorate the danger of cracking or chipping, especially when a variety of highly feldspathic materials are to be used with a wide array of different alloys.

SUMMARY

By the present invention, a method for firing dental prostheses of the dental porcelain fused to metal type is provided. After the application of a dental porcelain material to a metal part to form a veneer, the temperature of the veneer is raised from ambient temperature to a firing temperature. The firing temperature is maintained in the veneer for a time sufficient to provide fusion of the dental porcelain, thereafter the temperature of the veneer is reduced below the firing temperature to an intermediate temperature between the firing temperature and the ambient temperature, and this intermediate temperature is maintained in the veneer. In the preferred procedure after the intermediate temperature period, a further controlled reduction in the temperature of the veneer is provided before the final allowance of the drop in temperature to ambient temperature.

Other preferred aspects of the invention include providing for an intermediate temperature at the temperature approximating the maximum rate of crystallization of a crystalline phase, and providing a first reduction in temperature at a relatively rapid rate, and a second reduction in temperature at, during at least part of its progression, a relatively slow rate.

By another aspect of the invention, a furnace is provided having control means especially adapted to carry out the method in a preferred manner.

DESCRIPTION OF THE PREFERRED EMBODIMENT

Figure 1:
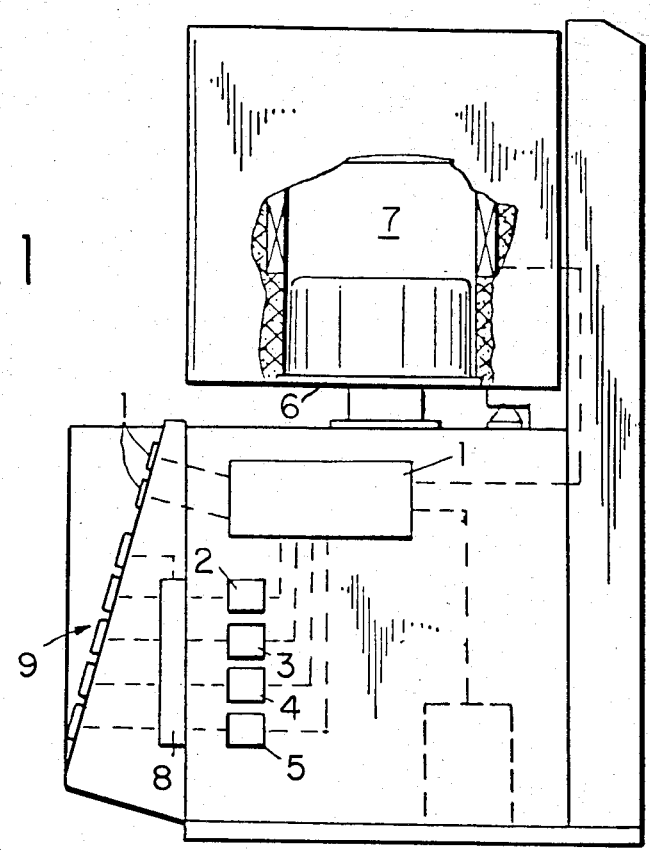
FIG. 1 is a schematic diagrammatic view of a furnace for carrying out the present invention.

The present invention in its preferred embodiment provides for phased cooling of the dental porcelain/metal prostheses that includes lowering the temperature from the firing temperature which is most preferably 950° to 980° C. for the most preferred porcelain material but could be lower or higher depending on the porcelain chosen. The cooling is preferably initially rapid for an 80° to 280° C. drop from the firing temperature. The drop is to an intermediate tempering temperature which is then maintained relatively constant for a period of time. The tempering temperature is preferably between 600° to 900° C. which is approximately the breadth of the temperature at which the maximum rate of crystallization occurs from the glass phase of the various preferred feldspathic dental porcelains. The intermediate temperature is preferably held for from 1 to 15 minutes, more preferably 3 to 10 minutes.

After the intermediate tempering temperature, preferably another rapid temperature reduction of 80° to 280° C. is carried out. This second rapid temperature reduction is followed by a slow controlled rate of temperature reduction for a period of final hardening or an annealing stage. This slow cooling annealing stage is preferably at the rate of between 1° C./minute and 50° C./minute. The slow cooling stage should extend down to 400° C. and would have a preferred range of 700° to 400° C., depending on the porcelain/metal characteristics. Obviously, there is some overlap in the ranges and this is because the ranges encompass porcelains and metals of different characteristics.

The tempering temperature should preferably be specifically set in most instances to provide or effect the optimum coefficient of expansion increase for the specific dental porcelain materials being used in order to match the coefficient of expansion of the particular metal employed. Once established and measured by sample replications, the temperature and cooling rates are programmed into the heat/cool cycle of a suitable dental porcelain furnace. It is believed that the controlled crystallization in the dental porcelain material that occurs during the tempering phase regulates the thermal expansion of the dental porcelain and by this means provides for a superior match of its thermal expansion to that of the chosen metal substrate. This results in reduced stress in the porcelain and greater adhesion or bonding with less chipping, checking, and cracking.

While the procedure of the the present invention can be carried out with furnaces of various designs, a particularly advantageous and preferred furnace is the one shown in U.S. patent application Ser. No. 462,916, filed Feb. 1, 1983, and assigned to the same assignee as the present invention, the contents of which U.S. patent application are incorporated herein by reference. The furnace is also the subject of a registered German design Gebrauchsmuster DE-GM No. 82 04 464. This is the furnace sold under the trademark, "MULTIMAT MC". In this furnace, the upper part containing the firing chamber is advantageously movable and the platform supporting the prostheses is located stationarily below or in the lower part of the furnace housing or firing chamber. This existing furnace of the previous patent application would, of course, be modified according to the present invention.

FIG. 1 represents the furnace in simple schematic manner, modified in accordance with the present invention. The control elements are contained within the lower housing which offers an entry keyboard 9 and a modular display. The furnace has a heatable firing chamber 7 with a firing platform 6 which fits into the socket at the bottom of the firing chamber. This platform is adjustable relative to the firing chamber in response to the commands of the control unit 1 to provide, in cooperation with the heating elements of the firing chamber, the time dependent temperature control for the manufacture of the dental prostheses. Elements or means are provided to select or set the following:

(a) the most favorable position of the platform within the socket of the firing chamber to provide the tempering step, (b) the intermediate tempering temperature, (c) the time of tempering, and (d) the annealing cooling rate(s) after finishing the tempering phase.

To this end, elements 2 to 5 are chosen to be programmable and operable in response to setting data fed to them by a microprocessor 8 in accordance with the specific alloy and/or dental porcelain chosen for a particular prostheses construction. The instructions are given to the microprocessor 8 by operation of the keyboard 9. The control unit 1 then operates the furnace to provide the necessary means to accomplish the requirement established by the present invention in a preferred manner.

The elements for controlling the furnace are programmable and automatic once programmed to provide the tempering phase according to the present invention, and subsequently, the slow cooling rate, all to be set depending upon the particular alloy porcelain veneer system chosen. It is essential that some means be provided and preferably that a programmed means be provided that will set and control the tempering phase and in the preferred furnace, at least in part, by the advantageous positioning of the firing platform within the socket of the firing chamber providing a substantially constant tempering temperature for a predetermined time and to then provide the desired slow annealing cooling rate following the completion of the tempering phase. The platform is incrementally lowered and raised in relation to the socket seat of the firing chamber in order to open and close the platform with the firing chamber and thereby assist in controlling the reduction in the temperature.

Figure 2:
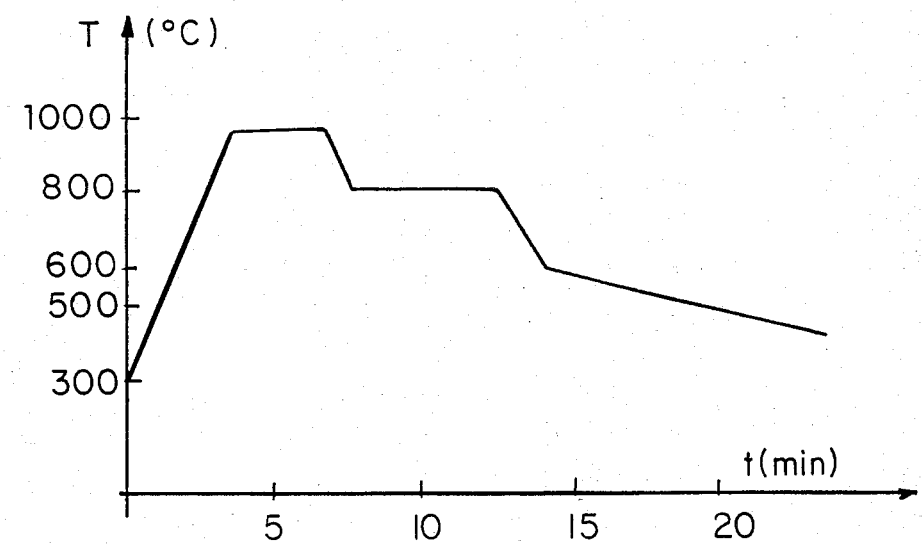
FIG. 2 is a graph representing the typical and tendentious course of the curve of the complete heat treatment according to the present invention.

The curve shown in FIG. 2 is specific to a non-precious alloy with a thermal expansion that is higher than $145 \times 10^{-7}$/K. veneered with a dental porcelain material specifically the "BIODENT-METALL-KERAMIK universal" of Example 1. The curve is, however, basically characteristic in its tendentious course for the present invention independently of the special alloy and is particularly illustrative of the cooling part of the curve which would normally start directly after the firing phase. This interruption of the cooling cycle and substantially rapid institution of the tempering range is characteristic of the present invention. This is not to say that the abrupt changes in the cooling rate shown in FIG. 2 need always be present.

OPERATION

In operation, the furnace, as described above, may be seen to have a heatable firing chamber 7, a firing platform 6, a firing platform socket which is where the firing platform closes with the firing chamber, and control means which are all of the control means associated with the lower housing of FIG. 1. The control means include a means for positioning the platform in the socket for a high temperature firing phase, a means for partially opening the firing platform from the socket and adjusting the temperature in the firing chamber to a reduced intermediate level, means for maintaining the temperature at the reduced intermediate level substantially constant for a set timed period, and means for reducing temperature at one or more substantially constant rates after the intermediate timed temperature period.

The control means includes a control unit 1 for positioning the firing platform in response to time activated commands. The control means is programmed by the keyboard 9 feeding the microcomputer 8. As contemplated, the preferred control means include means to select the following parameters, especially related to the present invention:

(a) the most favorable position of the platform within the socket to provide the intermediate temperature, (b) the intermediate temperature, (c) the time the intermediate temperature will be maintained, and (d) one or more substantially constant rates of reduction in temperature after the intermediate temperature. These selected parameters are each preferably controlled, in part, by separate programmable elements.

The furnace may be seen to provide an expedient means for carrying out the method of the present invention to produce a dental prostheses or restoration of the feldspathic dental porcelain fused to metal alloy substrate type. The method includes applying a feldspathic dental porcelain to a metal alloy substrate and forming a veneer, raising the temperature of the veneer from ambient temperature to a firing temperature of about 900° to about 980° C. in the firing chamber 7, maintaining the firing temperature in the veneer for a time sufficient to provide a fusing of said feldspathic dental porcelain in the firing chamber 7, thereafter reducing the temperature of the veneer by about 80° to about 280° C. to an intermediate tempering temperature of about 600° to about 900° C. between the firing temperature and ambient temperature by using the furnace control means and maintaining this intermediate temperature in the veneer preferably for 1 to 15 minutes. After the intermediate temperature, the temperature of the veneer is further reduced to ambient temperature. The intermediate temperature is preferably the temperature with about the maximum rate of crystallization out of the glass phase of the feldspathic dental porcelain which is normally between about 600° and about 900° C. The first reduction in temperature is preferably relatively rapid while the second reduction in temperature from the intermediate tempering temperature is, during at least part of its reduction, controlled preferably relatively slow using the furnace control means. The intermediate temperature is more preferably 3 to 10 minutes.

As used in this application, when it is recited that "the temperature of the veneer" has certain parameters, this temperature may be read by reading the temperature of the firing chamber in conventional manner, or when this is not appropriate by reading the temperature of the veneer itself.

The invention is further illustrated by the following examples:

EXAMPLES

Comparative Examples I and II were conducted wherein veneers were prepared using an alloy sold under the trademark "WIRON S" and a porcelain sold under the trademark "BIODENT-METALL-KERAMIK universal." The veneers were fired in a Multimat furnace of the type previously described, but not equipped with the features of the present invention. The furnace control was varied manually rather than by the programming of the present invention. The products of Examples I and II were tested according to the publication Dorsch, P.: Messmethode zur Spannungsberechnung in Metall/Porzellan-Verbundkorpern. Ber. Dtsch. Keram. Ges. 56, pages 328–331 (1979).

EXAMPLE I

A conventional procedure without the tempering phase and slow annealing cooling down was used. The product was simply removed from the furnace after firing and immediately exposed to ambient temperature. Using visual observation with the unaided eye, cracks were often observed in the prostheses. The stresses were determined to be 6,700 N/cm$^2$.

EXAMPLE II

The firing, tempering, and cooling procedure was that of FIG. 2. Again using visual observation with the unaided eye, no cracks or chipping was seen in the prostheses. The stresses were determined to be 900 N/cm$^2$.

While in accordance with the patent statutes what is at present considered to be the preferred embodiment of the invention has been described, it will obvious to those skilled in the art that numerous changes and modifications may be made therein without departing from the invention, and it is therefore aimed in the appended claims to cover all such equivalent variations as fall within the true spirit and scope of the invention.

It is claimed:

1. A method for preparing dental prostheses of the dental porcelain fused to metal type comprising, after the application of a dental porcelain material to a metal part to form a veneer, bringing the temperature of the veneer to a firing temperature, maintaining a firing temperature in the veneer for a time sufficient to provide a fusing of said dental porcelain, thereafter reducing the temperature of the veneer below said firing temperature by about 80° to about 280° C. to an intermediate temperature between the firing temperature and the ambient temperature, maintaining said intermediate temperature in the veneer, thereafter further reducing the temperature of the veneer to ambient temperature.

2. The method of claim 1 wherein the dental porcelain has a glass phase that is partially crystallized, and the intermediate temperature is the temperature with about the maximum rate of crystallization of said glass phase.

3. The method of claim 2 wherein the first said reduction in temperature is relatively rapid and the second said reduction in temperature is, during at least part of its progression, relatively slow.

4. The method of claim 1 wherein the intermediate temperature is a tempering temperature and said maintaining of said intermediate temperature is from about 1 to about 15 minutes.

5. The method of claim 4 wherein said intermediate temperature is about 600° to about 900° C.

6. The method of claim 5 wherein said dental porcelain is a feldspathic composition.

7. The method of claim 6 wherein the intermediate temperature is maintained from about 3 to about 10 minutes and the said second reduction in temperature is initially rapid and then at the rate of about 1° C./minute to about 50° C./minute until a temperature of about 400° C. is reached and then is uncontrolled by exposure to ambient temperature.

8. A method for preparing dental prostheses of the dental porcelain fused to metal type comprising, after the application of a dental porcelain material to a metal part to form a veneer, bringing the temperature of the veneer to a firing temperature, maintaining a firing temperature in the veneer for a time sufficient to provide a fusing of said dental porcelain, thereafter reducing the temperature of the veneer by about 80° to about 280° C. to an intermediate temperature between the firing temperature and the ambient temperature, maintaining said intermediate temperature in the veneer, and thereafter reducing the temperature of the veneer at the rate of about 1° C./minute to about 50° C./minute.

9. The method of claim 8 wherein the dental porcelain is of the feldspathic dental porcelain type and the metal is an alloy formed into a substrate, the temperature of said veneer is raised from ambient temperature to said firing temperature, said intermediate temperature is between about 600° to about 900° C.

10. The method of claim 9 wherein said intermediate temperature is the temperature with about the maximum rate of crystallization out of the glass phase.

11. The method of claim 10 wherein the reducing of the temperature to said intermediate temperature is relatively rapid and the reducing of the temperature from said intermediate temperature to the reducing temperature at the rate of about 1° C./minute to about 50° C./minute is relatively rapid.

12. The method of claim 11 wherein the intermediate temperature is maintained for about 1 to about 15 minutes and said reducing temperature at the rate of about 1° C./minute to about 50° C./minute is between a temperature of about 700° C. to about 400° C.

* * * * *